United States Patent [19]

Blackburn et al.

[11] Patent Number: 4,943,521

[45] Date of Patent: Jul. 24, 1990

[54] METHOD FOR EVALUATING MUTAGENICITY

[75] Inventors: Gary R. Blackburn, Washington Crossing, Pa.; Carl R. Mackerer, Pennington, N.J.; Ceinwen A. Schreiner, Meadowbrook, Pa.

[73] Assignee: Mobil Oil Corporation, New York, N.Y.

[21] Appl. No.: 18,119

[22] Filed: Feb. 24, 1987

[51] Int. Cl.$^5$ .................. C12Q 1/68; C12Q 1/02; C12Q 1/18

[52] U.S. Cl. .......................................... 435/6; 435/29; 435/34; 435/32; 435/879; 436/64

[58] Field of Search ............... 435/6, 29, 32, 34, 879, 435/33, 244, 248, 249, 250; 436/63, 64, 139

[56] References Cited

U.S. PATENT DOCUMENTS 4,499,187 2/1985 Blackburn et al. ............. 435/34

OTHER PUBLICATIONS

Prival, M. J., "The Salmonella Mutagenicity Assay, Promises and Problems", in *Cellular Systems for Toxicity Testing* (Williams, G. M. et al.), the New York Academy of Sciences, New York, N.Y., pp. 154–163 (1983).
Campbell et al., "Nitrated Polycyclic Aromatic ...", Carcinogenesis, vol. 2, No. 6, 559–565 (1981).
DiPaolo et al., "Nitration of Carcinogenic ...", Carcinogenesis, vol. 4, No. 3, pp. 357–359 (1983).
Rosenkrautz et al., "Mutagenicity ...", Mutation Research, 114 (1983), pp. 217–219 (1983).
Tokiwa et al., "1-6 Dinitropyrene: Mutagenicity ...", JNCl, vol. 73, No. 6, Dec. 1984, pp. 1359–1363 (1984).

*Primary Examiner*—Esther M. Kepplinger
*Assistant Examiner*—Toni R. Scheiner
*Attorney, Agent, or Firm*—Alexander J. McKillop; Charles J. Speciale

[57] ABSTRACT

A method for rapidly and reliably determining the potential carcinogenic activity of hydrocarbon mixtures which is especially useful for those of petroleum origin. A sample of the mixture is nitrated under conditions effective to convert the polynuclear aromatic hydrocarbons to their nitrated derivatives, and without separation of the nitrated components, the product is incubated with an inoculum of Salmonella typhimurium tester strain T98. The excessive production of revertant colonies is a measure of the mutagenic activity of the oil, and this measure is shown to correlate with dermal carcinogenic activity.

11 Claims, 3 Drawing Sheets

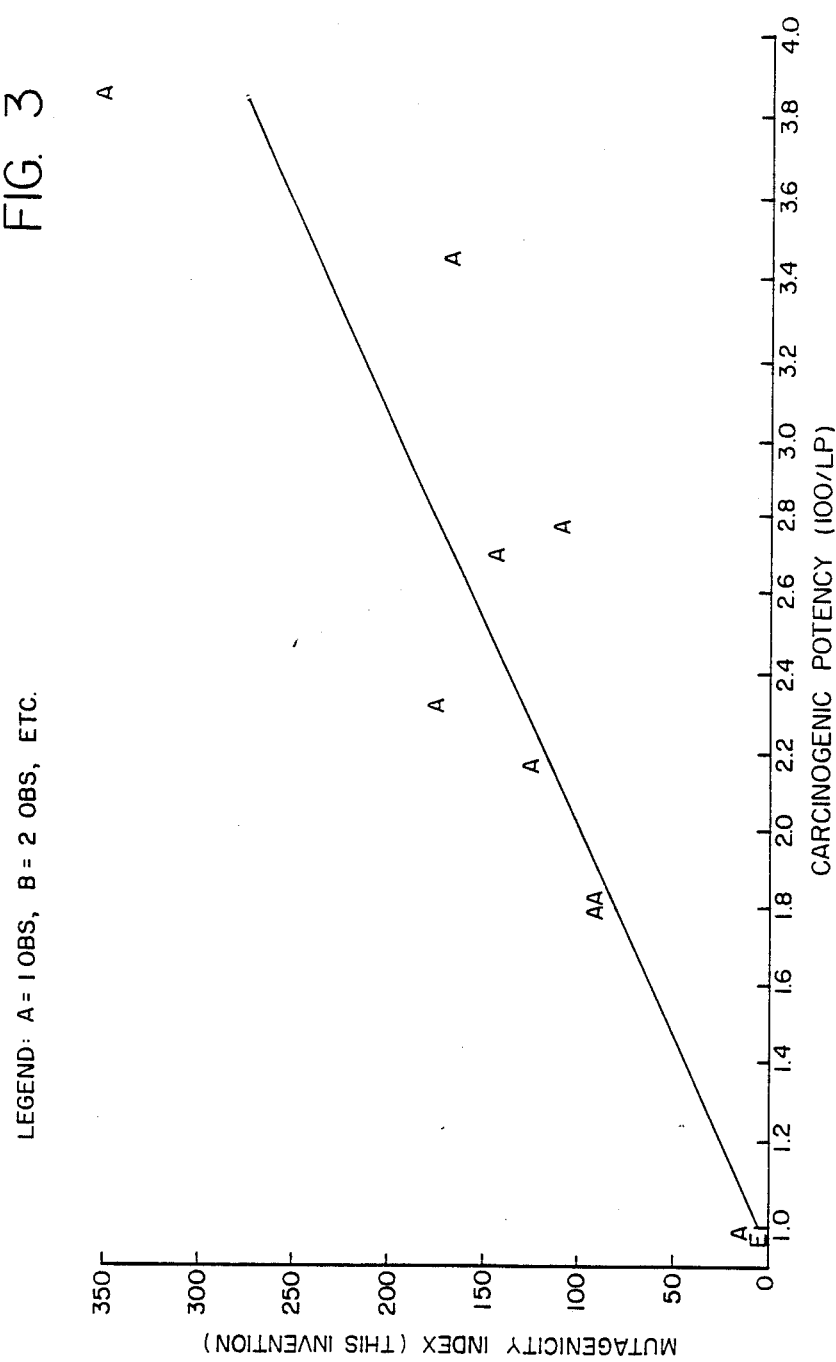

METHOD FOR EVALUATING MUTAGENICITY

FIELD OF THE INVENTION

This invention is broadly concerned with evaluating the carcinogenic activity of hydrocarbons. It is particularly concerned with evaluating the dermal carcinogenic activity, if any, of complex mixtures of hydrocarbons such as are encountered in a petroleum refinery, and of the fuels, lubricants and other products produced therefrom. It is more particularly concerned with a rapid method for assaying the mutagenic character of such hydrocarbon mixtures without isolation of the individual mutagenic components.

BACKGROUND OF THE INVENTION

The generally accepted method for evaluating the carcinogenic activity of petroleum products involves animal tests in which animals such as mice are exposed to the hydrocarbon by painting a portion of the skin repeatedly over a long period of time, and evaluating the tendency of such exposure to produce malignant growths. It is generally recognized that this test method requires seventy to eighty weeks of exposure to produce reliable results, and therefore that the method is not suited for situations in which a quick indication of potential carcinogenic activity is required.

In vitro mutagenic activity assays, such as, for example, the Salmonella Microsomal Activation Assay described by B. N. Ames, J. McCann, and E. Yamasaki in *Mutat. Research*, 31, 347-364 (1975), hereinafter referred to as the "Ames test", provide a rapid, inexpensive method for screening chemicals for carcinogenic potential. The entire content of this publication is incorporated herein by reference as if fully set forth. In general, the predictability of this assay with simple chemicals is good; validation studies have produced a 65-90% correlation between mutagenic activity and carcinogenic activity for many relatively pure compounds. However, the assay is unsuited to the testing of water insoluble complex mixtures, such as the complex hydrocarbon mixtures encountered in petroleum refinery streams. Attempts to use the Ames test procedure with such materials give results which are not reproducible and do not relate in a significant way to the known carcinogenic activity index for previously tested mixtures.

U.S. Pat. No. 4,499,187 to Blackburn et al. discloses a modification of the Ames test, hereinafter referred to as the "Modified Ames Test" suitable for use with complex hydrocarbon mixtures. The modification, in essence, involves the preparation of a DMSO (dimethylsulfoxide) extract of the sample being evaluated, and use of the DMSO extract instead of the sample itself in the Ames test together with an optimal amount of metabolic activator such as induced rat liver homogenate S-9. Detailed descriptions of the method for preparing the extract and for the assay itself are given in U.S. Pat. No. 4,499,187, the entire content of which is incorporated herein by reference. The Modified Ames Test, unlike the Ames test itself, provides a rapid and reproducible measure of the mutagenic activity of petroleum hydrocarbon mixtures, and the results of such assays strongly correlate with the carcinogenic activity index found for the mixtures by skin painting.

The Modified Ames Test described above is much more rapid than skin painting, requiring only about two to three days to complete an assay compared with 18 months. There remains a need, however, for a less labor-intensive and less costly assay.

BRIEF DESCRIPTION OF THE INVENTION

It has now been found that the mutagenicity of complex hydrocarbon mixture is advantageously determined by nitrating a sample of the mixture under relatively mild conditions, and subsequently assaying the mutagenicity in the Ames Test without use of a metabolic activator, all as more fully described hereinbelow. Because the nitration step eliminates the need for a liver metabolizing system, and performance of the assay is less labor-intensive, cost reduction is achieved without sacrifice of reliability and without the use of animal tissue. As will be shown hereinbelow, the method is particularly well suited to the assay of complex mixtures of hydrocarbons derived from petroleum and provides reliable predictability of the presence or absence of dermal carcinogenic activity for a mixture that boils above 500° F. The term "derived from petroleum" as used herein is intended to include petroleum fractions obtained by physical methods such as distillation, solvent extraction, and the like as well as such fractions that have been subjected to petroleum processes such as clay treating, hydrocracking, hydrofinishing, and the like.

BRIEF DESCRIPTION OF THE DRAWING

FIG. 3. Correlation of Carcinogenic Potency with Mutagenicity Index determined by method of the present invention.

PREFERRED EMBODIMENTS AND BEST MODE

Figure 1:
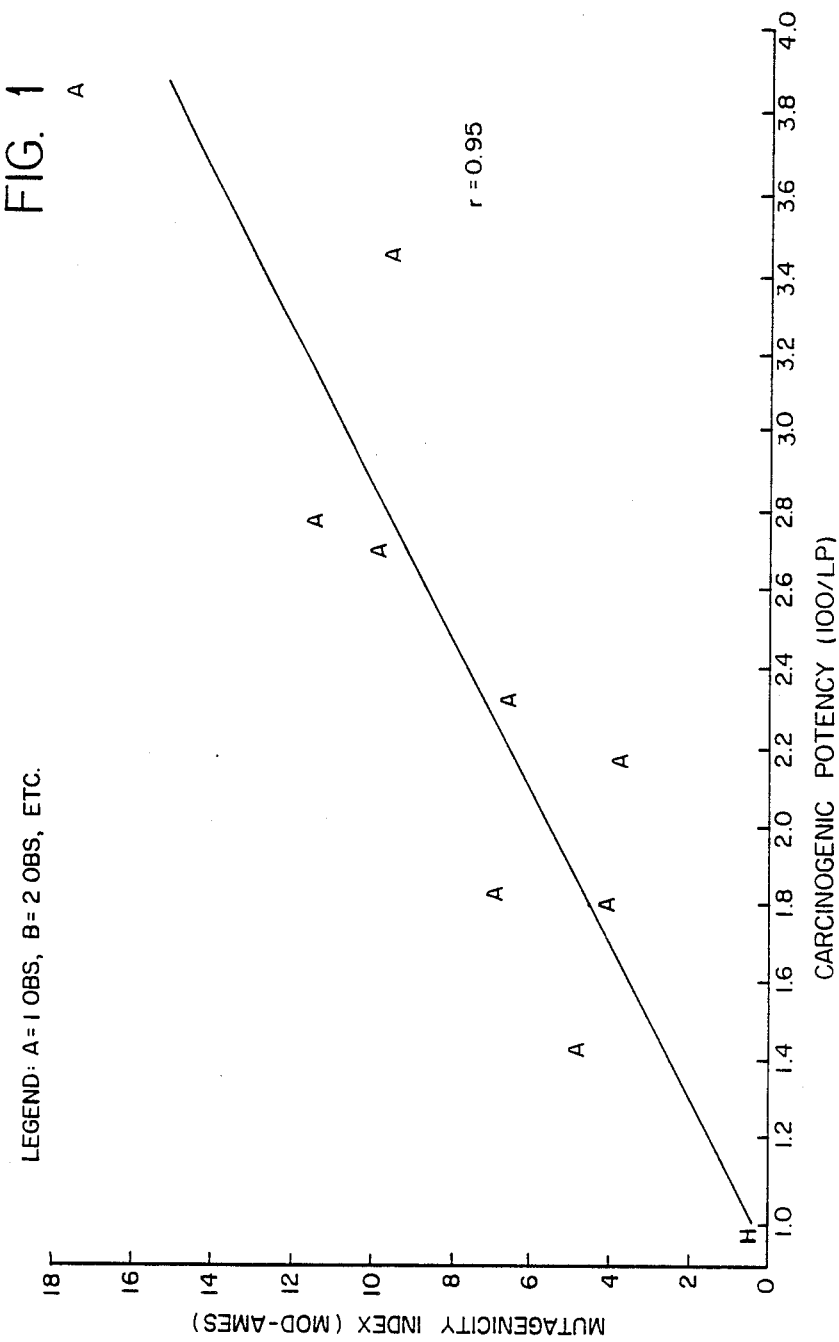
FIG. 1. Correlation of Carcinogenic Potency with Mutagenicity Index determined by the Modified Ames Test (Prior Art).

The preferred embodiments of the method of this invention including the best mode known to us will now be described.

A sample of the oil to be assayed is nitrated by the following procedure. To a known weight or volume of oil in about the 10 mg range, and contained in 0.1 ml of cyclohexane, is added 1 ml of 80% nitric acid of reagent grade or better. This mixture is incubated at 80° C. for two hours. It is then neutralized by adding 1 ml of 10 Molar sodium hydroxide. The neutralized mixture is cooled and 5 ml of dichloromethane is added, mixed, and allowed to stand for phase separation. The upper, aqueous phase is then carefully withdrawn and discarded, particular attention being given to avoid losses of any of the dichloromethane phase. After the initial separation, the dichloromethane phase is washed with 1 ml of water to remove some of the salts that are present in the residual aqueous phase, and the wash liquid removed and discarded. The dichloromethane phase is then evaporated and the recovered residue, which usually has a yellow to brown-red color, is dissolved in 2 ml of DMSO. This solution, referred to hereinbelow as the "test sample", is then assayed in the Ames Test, without addition of a liver metabolic activation system, and preferably with the use of the histidine-deficient mutant strain of *Salmonella typhimurium* TA98.

The Ames Test is conducted by introducing into a series of sterile capped culture tubes up to about eight different doses of the test sample. Whenever necessary, the test sample is diluted as required to insure accurate delivery. The doses, are selected to delimit the linear portion of the dose-response curve. To facilitate dosage selections, it is usually desirable to conduct a preliminary assay to approximately establish the boundaries of the dosages for the linear response range. To each tube the following are added: the appropriate volume of the test sample in DMSO; 0.5 ml of 0.2 Molar sodium phosphate buffer, pH 7.4; and 0.1 ml of *Salmonella typhimurium* TA98 broth culture ($1 \times 10^9$ cells per ml). Duplicate or triplicate tubes are prepared for each dose level. The cultures are incubated at 37° C. with agitation for 20 minutes, following which top agar (0.6% agar, 0.5% NaCl, 0.5 mM histidine-biotin) is added. The tubes are vortexed to ensure adequate mixing and the contents overlaid on 30 ml Vogel-Bonner minimal media plates. Plates are incubated inverted at 37° C. in the dark and revertant colonies are counted 48 hours later.

Mutagenic activity is assessed from the slope of the linear portion of the dose response curve that is obtained, and is reported as revertants per microliter of test sample.

The nitration procedure described above is very effective for purposes of the present invention, and is that which was used to establish the correlations generated by the Examples described below, unless otherwise noted. The Examples illustrate the preferred method of nitration. However, modifications of the nitration method may be used. For example, a sample may be nitrated at room temperature for 10 minutes with concentrated nitric acid (approximately 16 Molar) after which the nitrated mixture is neutralized and further treated as above to provide the test sample.

Although it is contemplated that the method of this invention may be used to reliably determine the mutagenicity of a complex mixture of hydrocarbons from any source, it is particularly useful for rapidly estimating the potential dermal carcinogenicity of a complex hydrocarbon mixture derived from petroleum. As will be shown below, there is a very strong correlation between the Mutagenicity Index derived by the method of this invention and carcinogenic potency for petroleum derived mixtures. The method of this invention is useful for petroleum derived mixtures substantially free of material boiling below 500° F., i.e. containing less than about 10 vol. % of material boiling below 500° F. For those that have a significant component boiling below 500° F., the correlation has been observed to deteriorate. With such mixtures, it is preferred to isolate the fraction boiling above 500° F. prior to nitration. All references made herein to boiling point are to be understood to refer to the boiling point as determined by ASTM Method D1160 (Distillation of Petroleum Products at Reduced Pressures), published by the American Society for Testing Materials, 1916 Race Street, Philadelphia, Penna.

Although DMSO is the presently preferred solvent for the nitrated material, it is contemplated that other solvents such as approved for use in the Ames Assay and effective in solubilizing the nitrated oil also may be used.

Although the histidine-deficient *Salmonella typhimurium* tester strain TA98 originally developed by B. N. Ames at the University of California, Berkelely, is particularly preferred, it is contemplated that other histidine-deficient strains of the organism such as TA100 may be useful.

This invention will now be illustrated by examples. The examples, however, are not to be construed as limiting the scope of the invention, which scope is determined by this entire specification including the appended claims.

EXAMPLES

Example 1

A data base was established using a series of twenty-one different petroleum oils and by-product extracts. These all boiled above about 500° F., and all but Sample No. 5 boiled within the range of about 500° F. to 1000° F. Sample No. 5, the hydrotreated bright stock extract, contained material which boiled above 1000° F. Table I provides a description for each of the twenty-one oils.

Each of the oil samples was evaluated for mutagenicity by the Modified Ames Test and by the method of this invention, and the Mutagenicity Index determined from the slope of the linear portion of the dose-response curve, as described above. Table II summarizes the results of the Mutagenicity Tests, and also the results of skin painting tests in terms of the observed LP (latent period) i.e. the average number of weeks elapsed before the development of a tumor, the number of animals that developed tumors, and the Carcinogenic Potency calculated as 100/LP. Oils that produced no tumors in 100 weeks are arbitrarily assigned a Carcinogenic Potency = 1.00.

TABLE I

| Sample No. | Description |
|---|---|
| 1 | Hydrotreated Machine Oil Extract |
| 2 | Hydrotreated Machine Oil Extract |
| 3 | Hydrotreated Machine Oil Extract |
| 4 | Hydrotreated Machine Oil Extract |
| 5 | Hydrotreated Bright Stock Extract |
| 6 | Furfural Extracted Naphthenic Distillate |
| 7 | Technical White Oil ($SO_2$ Extracted/Hydrofinished) |
| 8 | Furfural Extracted/Ferrofined Paraffinic Distillate |
| 9 | Mildly Furfural Extracted/Polished Paraffinic Distillate |
| 10 | Light Medicinal Oil BP |
| 11 | Furfural Extracted/Polished Paraffinic Distillate |
| 12 | Distillate Aromatic Extract |
| 13 | $SO_2$/Benzene Extracted, Ferrofined Paraffinic Distillate |
| 14 | Acid/Earth Treated Naphthenic Distillate |
| 15 | $SO_2$ Extracted Napthenic Distillate |
| 16 | $SO_2$ Extracted, Earth Finished Naphthenic Distillate |
| 17 | Mildly Hydrotreated Naphthenic Distillate |
| 18 | Hydrotreated Neutralized Naphthenic Distillate |
| 19 | Hydrotreated Naphthenic Distillate |
| 20 | Low Viscosity Index Paraffinic Oil - Hydrotreated |
| 21 | Low Viscosity Index Paraffinic Oil - Hydrotreated |

TABLE II

| SAMPLE NO. | MUTAGENICITY INDEX, MODIFIED AMES | MUTAGENICITY INDEX, NITRATED MATERIAL | LATENT PERIOD (LP) (WEEKS) | NUMBER ANIMALS WITH TUMOR(S) | CARCINOGENIC POTENCY, 100/LP |
| --- | --- | --- | --- | --- | --- |
| 1 | 9.7 | 140 | 37 | 22 | 2.70 |
| 2 | 11.0 | 106 | 36 | 23 | 2.78 |
| 3 | 5.2 | 95 | 55 | 7 | 1.82 |
| 4 | 4.6 | — | 70 | 6 | 1.43 |
| 5 | 0.0 | — | — | 0 | 1.00 |
| 6 | 0.0 | 0 | — | 0 | 1.00 |
| 7 | 0.0 | 0 | — | 0 | 1.00 |
| 8 | 0.9 | 7 | 48 | 1 | 2.08 |
| 9 | 0.0 | — | — | 0 | 1.00 |
| 10 | 0.0 | 0 | — | 0 | 1.00 |
| 11 | 0.0 | 10 | — | 0 | 1.00 |
| 12 | 17.0 | 354 | 26 | 41 | 3.85 |
| 13 | 2.4 | 70 | 44 | 2 | 2.27 |
| 14 | 9.1 | 284 | 20 | 6 | 5.00 |
| 15 | 0.0 | 0 | 58 | 1 | 1.72 |
| 16 | 0.0 | 0 | — | 0 | 1.00 |
| 17 | 3.9 | 114 | 46 | 1 | 2.17 |
| 18 | 4.0 | 95 | 56 | 4 | 1.79 |
| 19 | 3.6 | 123 | 46 | 5 | 2.17 |
| 20 | 6.5 | 178 | 43 | 5 | 2.33 |
| 21 | 9.2 | 170 | 29 | 20 | 3.45 |

EXAMPLE 2
(Prior Art)

In this example the correlation of the Mutagenicity Index determined by the Modified Ames Test and the Carcinogenic Potency determined by skin painting are shown in FIG. 1. The calculated sample correlation coefficient for the relationship is 0.95. In this and subsequent examples, the least squares regression line and the sample correlation coefficient are computed by the conventional procedures as given, e.g., in *Statistics Manual*, Edwin L. Crow et al., pp 152-159, Dover Publications, New York, N.Y. (1956), incorporated herein by reference.

EXAMPLE 3

Figure 2:
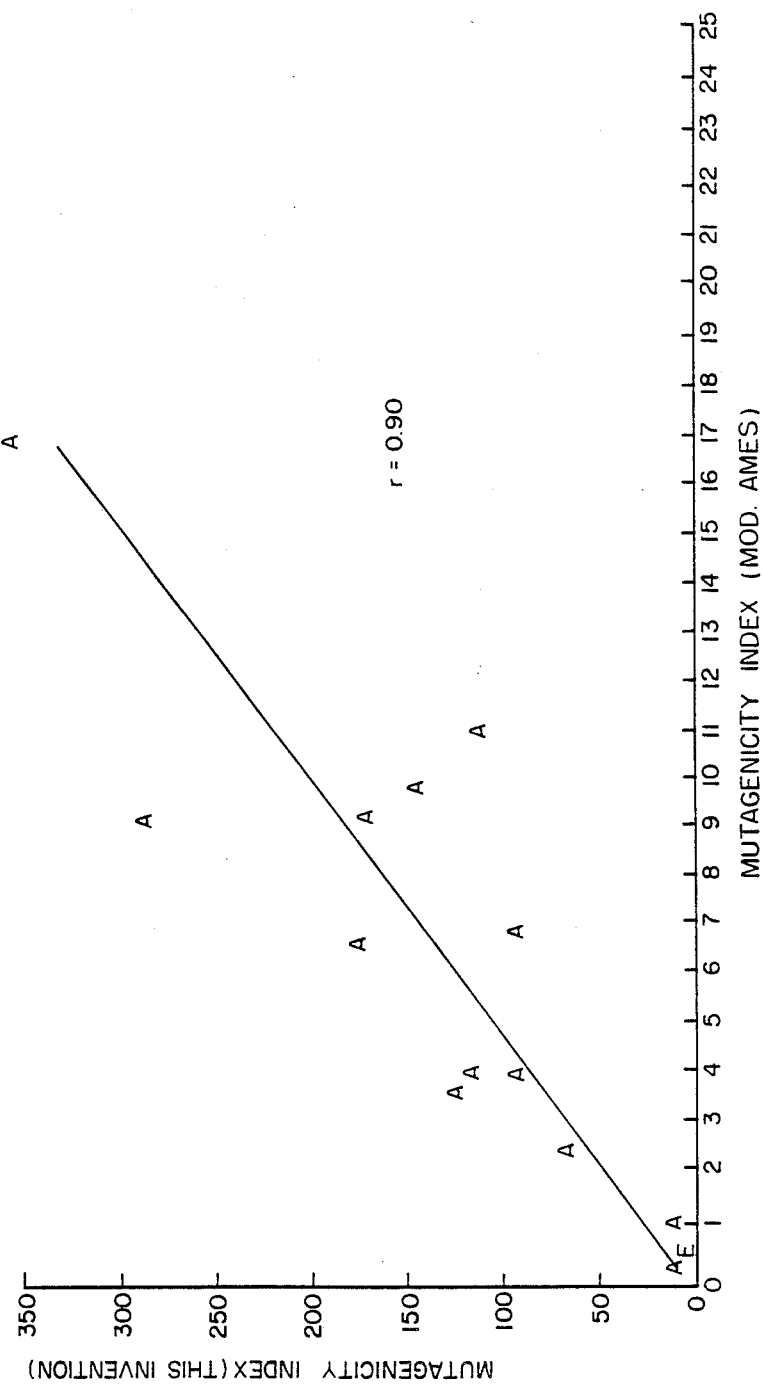
FIG. 2. Correlation of Mutagenicity Indices determined by method of the present invention and by Modified Ames Test.

The correlation of the Mutagenicity Index obtained by the method of this invention and shown in Table II with the Mutagenicity Index obtained with the Modified Ames Test is shown in FIG. 2. The calculated sample correlation coefficient is 0.90.

EXAMPLE 4

The correlation of the Mutagenicity Index obtained by the method of this invention and the Carcinogenic Potency by skin painting are shown in FIG. 3. The calculated sample correlation coefficient is 0.93.

It is evident from the foregoing examples that the method of this invention provides a test for mutagenicity which is simpler and more sensitive than the Modified Ames Test and yet provides highly significant prediction of carcinogenic potency. While not wishing to be bound by theory, it is believed that the observed correlations result from the mutagenic polynuclear aromatics contained in the oils evaluated.

Although the method of this invention has been exemplified with hydrocarbon mixtures derived from petroleum, it is contemplated that the method may be used with hydrocarbon mixtures derived from other fossil fuels such as coal and tar sands.

U.S. patent application Ser. No. 07/018,111 (Attorney's Docket Number 4207) filed on even date herewith provides a chemical method for evaluating the polynuclear aromatic content of hydrocarbon oils and the mutagenic activity for such oils.

What is claimed is:

1. A method for evaluating the relative mutagenic activity of a parent hydrocarbon mixture derived from petroleum, which method comprises:
    contacting a sample of said hydrocarbon mixture with nitric acid under conditions effective to nitrate the mutagenic components thereof;
    recovering from said nitric acid contacted hydrocarbon mixture a hydrocarbon mixture including nitrated mutagens;
    incubating without addition of a liver metabolic activation system an inoculum of a histidine deficient strain of *Salmonella typhimurium* in the presence of said nitrated mutagens;
    counting the number of revertant colonies so produced; and
    comparing said number with those obtained by the same steps from a reference series of different petroleum derived hydrocarbon mixtures of known mutagenic potency to determine the mutagenic potency of said nitrated mutagens, wherein the mutagenic potency of said nitrated mutagens correlates with the mutagenic potency of said parent hydrocarbon mixture.

2. The method described in claim 1 wherein several incubations are conducted with different amounts of said recovered hydrocarbon mixture, and wherein the determination of revertant colonies is made from the linear portion of the dose response curve.

3. The method described in claim 1 wherein said histidine-deficient strain of *Salmonella typhimurium* is TA98.

4. The method described in claim 2 wherein said histidine-deficient strain of *Salmonella typhimurium* is TA98.

5. The method described in claim 2 wherein said hydrocarbon mixture is substantially free of material boiling below 500° F.

6. The method described in claim 3 wherein said hydrocarbon mixture is substantially free of material boiling below 500° F.

7. The method described in claim 4 wherein said hydrocarbon mixture is substantially free of material boiling below 500° F.

8. A method for determining the relative dermal carcinogenic potency of a parent hydrocarbon mixture derived from petroleum, which method comprises:
contacting a sample of said hydrocarbon mixture with nitric acid under conditions effective to nitrate the mutagenic components thereof;
recovering from said nitric acid contacted hydrocarbon mixture a hydrocarbon mixture including nitrated mutagens;
incubating without addition of a liver metabolic activation system an inoculum of a histidine-deficient strain of *Salmonella typhimurium* in the presence of said nitrated mutagens;
counting the number of revertant colonies so produced; and
comparing said number with those obtained by the same steps from a reference series of different petroleum derived hydrocarbon mixtures of known dermal carcinogenic potency. to determine the dermal carcinogenic potency of said nitrated mutagens, wherein the dermal carcinogenic potency of said nitrated mutagens correlates with the dermal carcinogenic potency of said parent hydrocarbon mixture.

9. The method described in claim 8 wherein said hydrocarbon mixture is substantially free of material boiling below 500° F., and wherein said histidine-deficient strain of *Salmonella typhimurium* is TA98.

10. The method described in claim 1 wherein the numbers obtained from said reference series of hydrocarbon mixtures are reduced to a linear regression by conventional statistical methods, and said step of comparing is made with said regression.

11. The method described in claim 8 wherein the numbers obtained from said reference series of hydrocarbon mixtures are reduced to a linear regression by conventional statistical methods, and said step of comparing is made with said regression.

* * * * *